(12) United States Patent
Tsuyuki et al.

(10) Patent No.: US 7,215,426 B2
(45) Date of Patent: May 8, 2007

(54) DARK BOX APPARATUS FOR FLUOROSCOPY, FLUOROSCOPY SYSTEM, AND FLUOROSCOPY METHOD

(75) Inventors: Kei Tsuyuki, Hachioji (JP); Kazuhiko Osa, Hachioji (JP); Nobuyuki Nagasawa, Hino (JP)

(73) Assignee: Olympus Corporation (JP)

( * ) Notice: Subject to any disclaimer, the term of this patent is extended or adjusted under 35 U.S.C. 154(b) by 56 days.

(21) Appl. No.: 11/213,906

(22) Filed: Aug. 30, 2005

(65) Prior Publication Data

US 2006/0050276 A1 Mar. 9, 2006

(30) Foreign Application Priority Data

Sep. 3, 2004 (JP) .............................. 2004-257240

(51) Int. Cl.
*G01N 21/64* (2006.01)
(52) U.S. Cl. .................... 356/417; 356/318; 250/458.1
(58) Field of Classification Search ................ 356/317, 356/417; 250/458.1, 461.1
See application file for complete search history.

(56) References Cited

U.S. PATENT DOCUMENTS 5,331,171 A * 7/1994 Bongi ..................... 250/461.1

5,856,866 A * 1/1999 Shimizu et al. ............... 356/73

FOREIGN PATENT DOCUMENTS

| JP | 7-260694 | * 10/1995 |
| JP | 2002-369624 | 12/2002 |

* cited by examiner

*Primary Examiner*—F. L. Evans
(74) *Attorney, Agent, or Firm*—Kenyon & Kenyon LLP

(57) ABSTRACT

Noise in a fluorescence image acquired during fluoroscopy is eliminated to present a clear fluorescence image, and the relative positional relationship between the fluoroscopy unit and the specimen can be recognized even while fluoroscopy is in progress. A dark box apparatus for fluoroscopy includes: a dark-box main body enclosing a specimen and a fluoroscopy unit for illuminating the specimen with excitation light with a first spectral band and for detecting fluorescence with a second spectral band generated by the specimen; an illumination light source disposed in the dark-box main body to emit light with a third spectral band different from the first spectral band and the second spectral band; and an observation window disposed in the dark-box main body, the observation window being capable of transmitting light with a fourth spectral band which includes at least part of the third spectral band and does not include the first spectral band and the second spectral band.

11 Claims, 6 Drawing Sheets

DARK BOX APPARATUS FOR FLUOROSCOPY, FLUOROSCOPY SYSTEM, AND FLUOROSCOPY METHOD

BACKGROUND OF THE INVENTION

1. Field of the Invention

The present invention relates to dark box apparatuses for fluoroscopy, fluoroscopy systems, and fluoroscopy methods.

This application is based on Japanese Patent Applications No. 2004-257240, the contents of which are incorporated herein by reference.

2. Description of Related Art

As a technique for non-invasively examining the interior of a specimen, some known confocal microscopes or multiphoton-excitation microscopes employ a fluoroscopy method for illuminating a specimen with excitation light, such as a laser beam, to examine fluorescence generated by the specimen.

However, since fluorescence generated by a specimen is very weak, it is difficult to acquire a clear fluorescence image due to external noise if fluoroscopy is performed in the presence of extraneous light. For this reason, if fluoroscopy is to be performed in a darkroom, a specimen is first positioned with respect to the microscope apparatus under external light, and then the specimen is illuminated with excitation light with all extraneous light blocked to detect fluorescence emitted from the specimen.

Though in a totally different technical field, a so-called dark-place observation device for examining the influence of particular wavelengths of light upon plants in a place dark enough to prevent the plants from being affected by light is also known (e.g., see Japanese Unexamined Patent Application Publication No. 2002-369624).

For examination with these known dark-place observation devices, plants are first positioned in a dark box completely protected from extraneous light to prevent the plants from experiencing biological effects, such as gene expression, due to extraneous light, and then an infrared light source emitting infrared light with wavelengths that do not affect the plants and an infrared CCD camera are placed in the dark box to observe an image from the infrared CCD camera on a monitor outside the dark box.

If fluoroscopy is to be performed in a darkroom such that a specimen is first positioned with respect to the microscope apparatus under extraneous light and then the specimen is illuminated with excitation light with all extraneous light blocked to detect fluorescence emitted from the specimen, unsuccessful positioning of the specimen, such as a shift of the specimen from the desired examination position, may occur. In this case, the positional relationship between the microscope apparatus and the specimen needs to be re-adjusted. Thus, the positional relationship between the microscope and the specimen may need to be adjusted by feeling with the hands in a darkroom where extraneous light is blocked. This may cause the objective lens of the microscope apparatus to interfere with the specimen, possibly damaging the objective lens or the specimen. In addition, repeating the procedure of introducing extraneous light for positioning and then blocking the extraneous light again for examination is time-consuming and annoying.

BRIEF SUMMARY OF THE INVENTION

The present invention has been conceived in light of these circumstances, and it is an object of the present invention to provide a dark box apparatus for fluoroscopy, a fluoroscopy system, and a fluoroscopy method for eliminating noise in a fluorescence image acquired during fluoroscopy to present a clear fluorescence image and for checking the relative positional relationship between the fluoroscopy unit and the specimen even while fluoroscopy is in progress.

In order to achieve the above-described objects, the present invention provides the following solutions.

According to a first aspect of the present invention, a dark box apparatus for fluoroscopy includes: a dark-box main body enclosing a specimen and a fluoroscopy unit for illuminating the specimen with excitation light with a first spectral band and for detecting fluorescence with a second spectral band generated by the specimen; an illumination light source disposed in the dark-box main body to emit light with a third spectral band different from the first spectral band and the second spectral band; and an observation window disposed on the dark-box main body, the observation window being capable of transmitting light with a fourth spectral band which includes at least part of the third spectral band and does not include the first spectral band and the second spectral band.

According to this aspect, when fluoroscopy is to be performed by placing the specimen and the fluoroscopy unit in the dark-box main body and radiating excitation light with the first spectral band to detect fluorescence with the second spectral band emitted from the specimen, the illumination light source is operated in the dark-box main body to emit visible light with the third spectral band. Since the observation window provided in the dark-box main body can transmit light with the fourth spectral band including at least part of the third spectral band, part of light with the third spectral band reflected at the specimen and the fluoroscopy unit passes through the observation window and is observed by an external observer.

In other words, the observer can easily recognize the state of the specimen, the positional relationship between the specimen and the fluoroscopy unit, etc. in the dark-box main body with the aid of light with the third spectral band coming through the observation window. On the other hand, since the third spectral band differs from the first spectral band, even if light with the third spectral band is emitted in the dark-box main body, the fluorescent material of the specimen is not excited with the emitted visible light with the third spectral band. Furthermore, since the third spectral band differs from the second spectral band, light with the third spectral band emitted in the dark-box main body is not detected by the fluoroscopy unit, and hence noise in the acquired fluorescence image does not increase.

Since the observation window transmits light with the fourth spectral band, light with the fourth spectral band may enter the dark-box main body from outside the dark-box main body. However, since the fourth spectral band does not include the first spectral band and the second spectral band, the fluorescent material is not excited by light entering the dark-box main body or noise in the fluorescence image does not increase, just like in the above-described case. On the other hand, the observation window transmits at least part of other light with the third spectral band from outside the dark-box main body. This transmitted light can be used as illumination light along with the light from the illumination light source.

In the above-described aspect, it is preferable that the illumination light source be disposed at a location such that the illumination light source is not directly visible from outside through the observation window.

In this manner, the observer observing from outside the dark-box main body through the observation window does not look directly at the illumination light source. This prevents light of the illumination light source from dazzling the observer. More specifically, the illumination light source may be provided out of the field of view of the observation window or alternatively, a baffle plate etc. may be provided to prevent light from the illumination light source from directly reaching the observation window.

According to a second aspect of the present invention, a dark box apparatus for fluoroscopy includes: a dark-box main body for blocking entry of extraneous light by enclosing a specimen and a fluoroscopy unit for illuminating the specimen with excitation light with a first spectral band and for detecting fluorescence with a second spectral band generated by the specimen; an illumination light source disposed in the dark-box main body to emit light with a third spectral band different from the first spectral band and the second spectral band; a photography unit disposed in the dark-box main body to photograph the specimen illuminated by the illumination light source and the fluoroscopy unit; and an image display unit disposed outside the dark-box main body to display an image acquired by the photography unit.

According to this aspect, when the specimen and the fluoroscopy unit are placed in the dark-box main body and excitation light with the first spectral band is radiated to perform fluoroscopy for detecting fluorescence with the second spectral band emitted from the specimen, the illumination light source is operated in the dark-box main body to radiate light with the third spectral band. Light with the third spectral band is radiated onto the specimen and the fluoroscopy unit and is photographed by the photography unit provided in the dark-box main body. An acquired image is displayed on the image display unit outside the dark-box main body. The observer can easily recognize the state of the specimen, the positional relationship between the specimen and the fluoroscopy unit, etc. by observing on the image display unit the specimen and the fluoroscopy unit illuminated with light with the third spectral band.

On the other hand, since the third spectral band differs from the first spectral band, even if light with the third spectral band is emitted in the dark-box main body, the fluorescent material of the specimen is not excited with the emitted light with the third spectral band. Furthermore, since the third spectral band differs from the second spectral band, light with the third spectral band emitted in the dark-box main body is not detected by the fluoroscopy unit, and hence noise in the acquired fluorescence image does not increase.

In the above-described aspect, it is preferable that the illumination light source be disposed at a location such that light emitted from the illumination light source is not directly incident upon the photography unit.

In this manner, an image acquired by the photography unit can be free of noise, such as flare, due to light from the illumination light source. Therefore, light from the illumination light source does not interfere with the observation. More specifically, the illumination light source may be provided out of the field of view of the photography unit or alternatively, a baffle plate etc. may be provided to prevent light from the illumination light source from being directly incident upon the photography unit.

In the above-described aspect, a camera including the photography unit and the image display unit may be provided on a wall surface of the dark-box main body such that the photography unit faces inward and the image display unit faces outward.

In this manner, an image which would appear if the interior of the dark box were observed through the observation window can be displayed on the image display unit.

In the above-described aspect, a bellows member may be provided between the wall surface of the dark-box main body and the camera such that the bellows member supports the camera so that the camera is movable relative to the wall surface.

In this manner, the image display range on the image display unit can easily be adjusted by moving the camera with respect to the wall surface through deformation of the bellows member.

In the above-described aspect, the illumination light source may include a wavelength-switching mechanism for switching a spectral band of emitted light.

When examination is to be performed using the fluoroscopy unit with the wavelength of the excitation light switched, the wavelength-switching mechanism is operated to switch the spectral band of light to be emitted by the illumination light source, thereby allowing the wavelength of the excitation light to be selected more flexibly.

According to a third aspect of the present invention, a fluoroscopy system includes: a fluoroscopy unit for illuminating a specimen with excitation light with a first spectral band and for detecting fluorescence with a second spectral band generated by the specimen; and one of the above-described dark box apparatuses for fluoroscopy, wherein the dark-box main body includes: a door for opening and closing the dark-box main body; an open/closed sensor for detecting an open/closed state of the door; and an excitation-light control section for stopping emission of excitation light from the fluoroscopy unit when the open/closed sensor detects that the door is opened.

According to this aspect, the specimen and the fluoroscopy unit are placed in the dark-box main body, the door is closed, excitation light with the first spectral band is radiated onto the specimen in the fluoroscopy unit, and fluorescence with the second spectral band emitted from the specimen is detected to perform fluoroscopy. If the door is opened for some reason during fluoroscopy, the open/closed sensor detects an open state of the door and emission of excitation light in the fluoroscopy unit is stopped by the operation of the excitation light control section. As a result, the excitation light is prevented from leaking from the dark box.

Furthermore, when the open/closed sensor detects a closed state of the door, excitation light is emitted by the operation of the excitation light control section. As a result, fluoroscopy is performed while light serving as noise from outside the dark box is blocked. This provides a clear fluorescence image with less noise.

According to a fourth aspect of the present invention, a fluoroscopy system includes: a fluoroscopy unit for illuminating a specimen with excitation light with a first spectral band and for detecting fluorescence with a second spectral band generated by the specimen; and one of the above-described dark box apparatuses for fluoroscopy, wherein the dark-box main body includes: a door for opening and closing the dark-box main body; an open/closed sensor for detecting an open/closed state of the door; and an operation control section for decreasing an operation speed of the fluoroscopy unit when the open/closed sensor detests that the door is closed.

According to this aspect, the door of the dark-box main body is opened, the specimen is positioned with respect to the fluoroscopy unit, preparations are made for rough alignment of the focal position of the fluoroscopy unit, and then the door is closed to arrange the specimen and the fluoroscopy unit in the dark-box main body. In this state, fluoroscopy is performed by radiating excitation light with the first spectral band onto the specimen in the fluoroscopy unit while the positional relationship between the specimen and the fluoroscopy unit is finely adjusted under light with the third spectral band from the illumination light source to detect fluorescence with the second spectral band emitted from the specimen. In this case, according to the present invention, the operation of the operation control section causes the fluoroscopy unit to operate at a lower operation speed while the open/closed sensor detects a closed state of the door compared to when the open/closed sensor detects an open state of the door. As a result, it is possible to reduce the risk of the fluoroscopy unit mistakenly interfering with the specimen in the dark-box main body because only limited information is obtained through the observation window or the image display unit. Therefore, damage to the fluoroscopy unit and the specimen can be avoided.

According to a fifth aspect of the present invention, a fluoroscopy method for emitting excitation light with a first spectral band from a fluoroscopy unit onto a specimen and for examining fluorescence with a second spectral band emitted from the specimen, the method includes steps of: enclosing the specimen and the fluoroscopy unit with a dark box; emitting light with a third spectral band different from the first spectral band and the second spectral band in the dark box; and manipulating the specimen or the fluoroscopy unit from outside the dark box while observing light with the third spectral band outside the dark box through an observation window, disposed in the dark box, capable of transmitting light with a fourth spectral band which includes at least part of the third spectral band and does not include the first spectral band and the second spectral band or through a photography unit disposed in the dark box.

According to this aspect, the fluoroscopy unit and the specimen are irradiated with light with the third spectral band to carry out examination through the observation window or the photography unit. Therefore, the positional relationship between the fluoroscopy unit and the specimen can easily be recognized in the dark box for reliable operation without disturbing fluoroscopy with the fluoroscopy unit. Therefore, blind operation is eliminated, and hence an annoying repeated procedure of turning ON and OFF the illuminating light in the darkroom can be avoided.

According to the present invention, since the fluoroscopy unit and the specimen are irradiated with light with the third spectral band different from the first and second spectral bands for examination through the observation window or the photography unit, the positional relationship between the fluoroscopy unit and the specimen can easily be recognized in the dark box for reliable operation without disturbing fluoroscopy with the fluoroscopy unit. Therefore, blind operation is eliminated, and hence an annoying repeated procedure of turning ON and OFF the illuminating light in the darkroom can be avoided.

DETAILED DESCRIPTION OF THE INVENTION

A dark box apparatus for fluoroscopy 1 according to a first embodiment of the present invention will now be described with reference to FIGS. 1 and 2.

Figure 1:
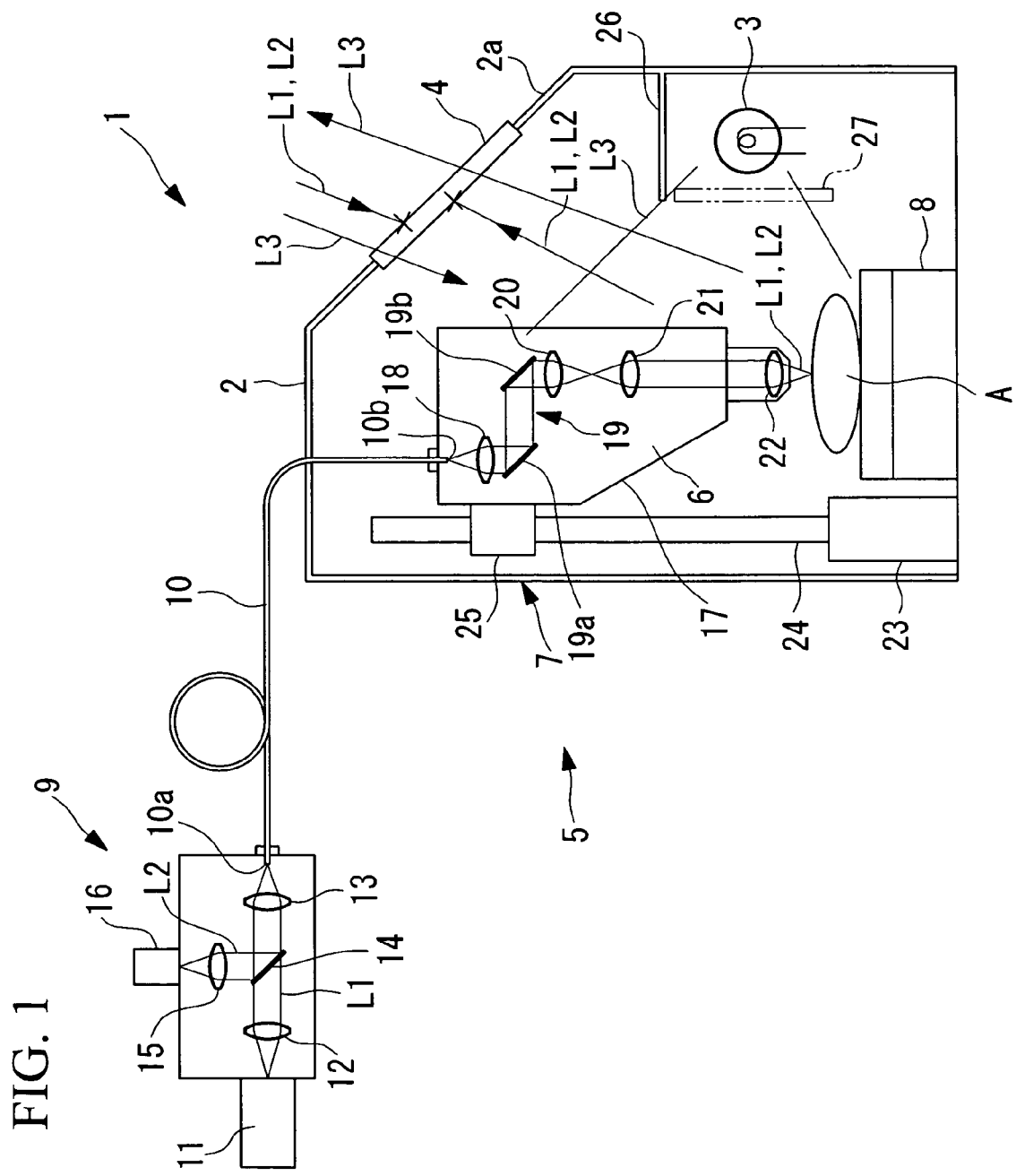
FIG. 1 is a longitudinal sectional view of a dark box apparatus for fluoroscopy according to a first embodiment of the present invention.

Referring to FIG. 1, the dark box apparatus for fluoroscopy 1 according to this embodiment includes a dark-box main body 2; an illumination light source 3 arranged in the dark-box main body 2; and an observation window 4 arranged in a wall surface 2a of the dark-box main body 2.

The above-described dark-box main body 2 is a box member composed of a material blocking light of all wavelengths, and is large enough to completely contain an examination head 6 of a fluoroscopy unit 5, to be described below; a raising-and-lowering mechanism 7 for raising and lowering the examination head 6; a specimen A; and a stage 8 holding the specimen A for moving the specimen A two-dimensionally in the horizontal direction or tilting the specimen A.

As shown in FIG. 1, the fluoroscopy unit 5 includes an optical unit 9; the examination head 6; and an optical fiber 10 for connecting the optical unit 9 and the examination head 6.

The optical unit 9 includes an excitation light source 11 emitting excitation light L1 with a first spectral band B1 (e.g., a wavelength of 545 nm), such as a laser beam; a collimating lens 12 for converting the emitted excitation light L1 into collimated light; a coupling lens 13 for focusing the excitation light L1 converted into collimated light onto an end surface 10a of the optical fiber 10; a dichroic mirror 14 for separating fluorescence L2 with a second spectral band B2 (e.g., a wavelength of 550 nm) from return light returning through the optical fiber 10; a focusing lens 15 for focusing the separated fluorescence L2; and a photodetector 16 for detecting the focused fluorescence L2. The photodetector 16 is realized by, for example, a photomultiplier tube (PMT).

The examination head 6 includes a casing 17 which includes a collimating lens 18 for converting the excitation light L1 from the excitation light source 11 into collimated light; an optical-scanning section 19 performing two-dimensional scanning of the collimated light transmitted from the collimating lens 18; a pupil-projection lens 20 for forming an intermediate image by focusing the scanned excitation light L1; and an imaging lens 21 for converting the excitation light L1 of the intermediate image into collimated light. The casing 17 further includes an objective lens 22 for focusing the excitation light L1 from the imaging lens 21 to re-form an image at a predetermined focal position.

The optical-scanning section 19 is realized by, for example, so-called proximity galvano mirrors, which are two galvano mirrors 19a and 19b arranged so as to oppose each other and which are rockable about mutually orthogonal axes.

The raising-and-lowering mechanism 7 supporting the examination head 6 such that the examination head 6 can be raised and lowered includes a raising-and-lowering slider 25 which can be raised and lowered by a driving device (not shown) in a support stand 24 extending vertically from a base 23. The driving device can be operated from outside the dark-box main body 2 through remote operation.

The above-described illumination light source 3 is realized by, for example, an argon laser light source emitting visible light L3 with a third spectral band B3 in the vicinity of, for example, 458 nm.

As shown in FIG. 1, the observation window 4 is provided on a tilted surface in the front of the dark-box main body 2, namely, on the tilted surface constituting part of the wall surface 2a of the dark-box main body 2. Through the observation window 4, the examination head 6 of the fluoroscopy unit 5, which is arranged on the other side of the wall surface 2a of the dark-box main body 2, and the specimen A are in the field of view.

Figure 2:
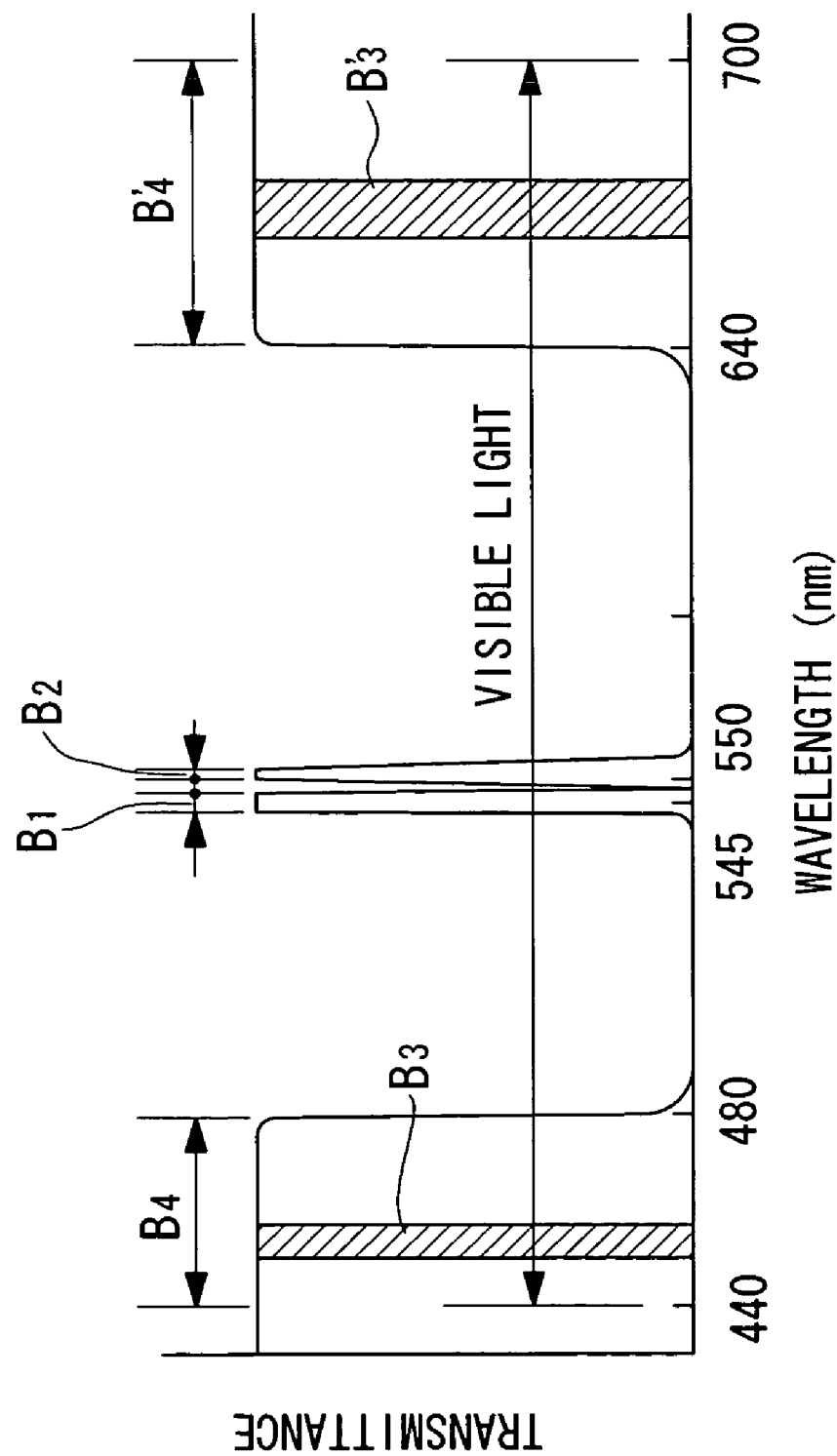
FIG. 2 is a diagram depicting a spectral band of fluorescence in response to light from an illumination light source of the dark box apparatus for fluoroscopy shown in FIG. 1 and the transmittance characteristic of an observation window.

Referring to FIG. 2, the observation window 4 blocks the excitation light L1 with the first spectral band B1 emitted from the excitation light source 11 of the fluoroscopy unit 5 and the fluorescence L2 with the second spectral band B2 emitted from the specimen A, while transmitting the visible light L3 with the third spectral band B3 emitted from the illumination light source 3. In short, the observation window 4 is characterized by transmitting light with wavelengths shorter than 480 nm and blocking light with wavelengths of 480 nm and longer.

In this embodiment, the dark-box main body 2 further includes a baffle plate 26 arranged between the observation window 4 and the illumination light source 3. The baffle plate 26 is arranged to block the illumination light source 3 from the observation window 4, thus preventing the illumination light source 3 from being viewed directly through the observation window 4.

A fluoroscopy method using the dark box apparatus for fluoroscopy 1 according to this embodiment, with the above-described structure, will now be described.

In order to perform fluoroscopy of the specimen A using the dark box apparatus for fluoroscopy 1 according to this embodiment, first the excitation light source 11 of the fluoroscopy unit 5 is turned OFF, the specimen A is immobilized on the stage 8 outside the dark-box main body 2, and the raising-and-lowering mechanism 7 is operated to roughly position the objective lens 22 of the examination head 6 with respect to the specimen A. In this state, the specimen A, the examination head 6, the stage 8, and the raising-and-lowering mechanism 7 are placed in the dark-box main body 2. The dark-box main body 2 may be constructed so as to enclose the specimen A, the examination head 6, etc. Alternatively, the dark-box main body 2 may have a door, as described in another embodiment later, so that the examination head 6 and other members are enclosed by closing this door.

Next, the illumination light source 3 is operated to emit the visible light L3 with the third spectral band B3 in the dark-box main body 2. The visible light L3 with the third spectral band B3 is radiated onto the objective lens 22 of the examination head 6 in the dark-box main body 2 and the specimen A opposed to the objective lens 22. Part of the visible light L3 with the third spectral band B3 reflected at the objective lens 22 and the specimen A goes out of the dark-box main body 2 through the observation window 4.

Therefore, outside the dark-box main body 2, the observer can observe the visible light L3 with the third spectral band B3 transmitted through the observation window 4 to clearly learn the positional relationship between the objective lens 22 and the specimen A, as well as the state of the specimen A in the dark-box main body 2.

Based on this positional relationship between the objective lens 22 and the specimen A observed through the observation window 4, the observer operates the raising-and-lowering mechanism 7 and the stage 8 through remote operation from outside the dark-box main body 2 to adjust the positional relationship.

Next, the fluoroscopy unit 5 is operated to emit the excitation light L1 with the first spectral band B1 from the excitation light source 11. The excitation light L1 is guided into the examination head 6 in the dark-box main body 2 via the optical fiber 10. The excitation light L1 guided into the examination head 6 is converted into collimated light by the collimating lens 18, is two-dimensionally scanned by the optical-scanning section 19, and is re-focused onto the specimen A through the pupil-projection lens 20, the imaging lens 21, and the objective lens 22.

When the specimen A is irradiated with the excitation light L1, fluorescent material in the specimen A or a fluorescent agent that has been pre-administered to the specimen A is excited to emit the fluorescence L2 with the second spectral band B2. The emitted fluorescence L2 enters an end surface 10b of the optical fiber 10 through the objective lens 22, the imaging lens 21, the pupil-projection lens 20, the optical-scanning section 19, and the collimating lens 18.

Since the end surface 10b of the optical fiber 10 is arranged to have a conjugate positional relationship with the focal position of the objective lens 22, only the fluorescence L2 generated near the focal position of the objective lens 22, from among the fluorescence L2 returning from the specimen A, enters the end surface 10b of optical fiber 10 and is returned to the optical unit 9. The fluorescence L2 returned to the optical unit 9 is converted into collimated light by the coupling lens 13, separated from the light path by the dichroic mirror 14, focused by the focusing lens 15, and finally detected by the photodetector 16.

The excitation light L1 is two-dimensionally scanned at the focal position of the objective lens 22 through the operation of the optical-scanning section 19. In this manner, a clear two-dimensional fluorescence image can be acquired by detecting the fluorescence L2 from each position of the specimen A with the photodetector 16.

According to the dark box apparatus for fluoroscopy 1 of this embodiment, the third spectral band B3 of the visible light L3 from the illumination light source 3 differs from the first spectral band B1 of the excitation light L1 and the second spectral band B2 of the fluorescence L2. Therefore, even if the visible light L3 is emitted from the illumination light source 3 onto the specimen A during fluoroscopy, the fluorescent material in the specimen A is not excited. Furthermore, even if the visible light L3 with the third spectral band B3 reflected at the specimen A enters the detection light path of the fluorescence L2 through the objective lens 22, the visible light L3 cannot be deflected by the dichroic mirror 14. Thus, the visible light L3 does not enter the photodetector 16, and is not therefore detected as noise by the photodetector 16.

In short, the visible light L3 with the third spectral band B3 from the illumination light source 3 does not interfere with fluoroscopy, and hence can continue to be emitted during fluoroscopy, as well as at a preliminary stage of fluoroscopy. Since the observation window 4 can transmit the visible light L3 with the third spectral band B3, the visible light L3 with the third spectral band B3 is likely to enter the dark-box main body 2 through the observation window 4 from outside the dark-box main body 2. However, since the visible light L3 with the third spectral band B3 does not interfere with fluoroscopy as described above, the visible light L3 does not adversely affect fluoroscopy even if it enters the dark-box main body 2 through the observation window 4.

During fluoroscopy, the observer may wish to adjust the positional relationship between the specimen A and the fluoroscopy unit 5 while checking on the monitor (not shown) a fluorescence image acquired with the photodetector 16. For this purpose, the observer can perform adjustment work while clearly seeing, through the observation window 4, the specimen A and the examination head 6 which are brightly illuminated with the visible light L3 with the third spectral band B3 emitted from the illumination light source 3.

Consequently, unlike with the known method, blind adjustment in a darkroom is not required according to this embodiment, and hence an annoying repeated procedure of turning ON and OFF the illuminating light in the darkroom can be avoided.

In the dark box apparatus for fluoroscopy 1 according to this embodiment, the baffle plate 26 provided in the darkbox main body 2 prevents the visible light L3 emitted from the illumination light source 3 from directly reaching the observation window 4. Therefore, the observer is prevented from looking directly at the illumination light source 3. Because of this, the observer is not too dazzled to see the interior of the dark-box main body 2, which would occur if the observer looked directly at the illumination light source 3.

Furthermore, according to this embodiment, the optical unit 9 including the excitation light source 11 is arranged outside the dark-box main body 2. For this reason, the temperature in the dark-box main body 2 is prevented from rising due to heat emission of the excitation light source 11. This is advantageous in preventing the specimen A from becoming dry and maintaining stable examination conditions.

Although this embodiment has been described by way of the third spectral band B3, which is shorter than the first spectral band B1 of the excitation light L1 and the second spectral band of the fluorescence L2, alternatively, a spectral band B3' that is longer than the first spectral band B1 and the second spectral band B2 may be adopted, as shown in FIG. 2. In this case, it is sufficient to set the transmittance characteristic of the observation window 4 to cover a spectral band including the spectral band B3'.

In addition, the illumination light source 3 may be provided with a filter-switching unit 27 for switching the spectral band B3 of the visible light L3 to be emitted.

When examination is to be performed using the fluoroscopy unit 5 with the wavelength of the excitation light L1 switched, the filter-switching unit 27 is operated to switch the spectral band B3 of the visible light L3 to be emitted by the illumination light source 3, thereby allowing the wavelength of the excitation light L1 to be selected more flexibly.

A dark box apparatus for fluoroscopy 30 according to a second embodiment of the present invention will now be described with reference to FIG. 3.

The same components in this embodiment as those used in the dark box apparatus 1 according to the first embodiment shown in FIG. 1 are denoted by the same reference numerals, and thus will not be described.

Figure 3:
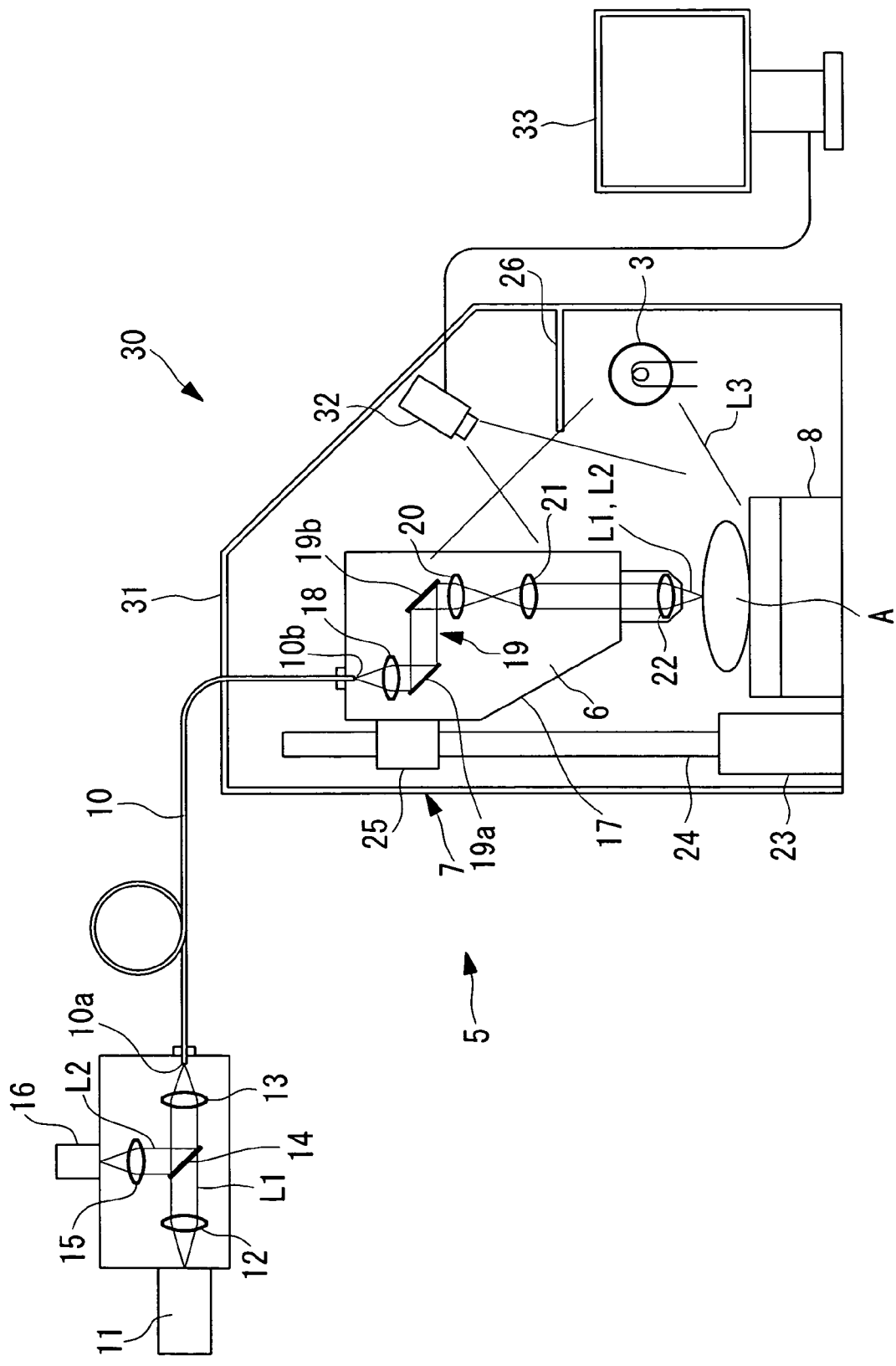
FIG. 3 is a longitudinal sectional view of a dark box apparatus for fluoroscopy according to a second embodiment of the present invention.

Referring to FIG. 3, the dark box apparatus for fluoroscopy 30 according to this embodiment includes a dark-box main body 31 in place of the dark-box main body 2 of the dark box apparatus for fluoroscopy 1 according to the first embodiment. The dark-box main body 31 is not provided with the observation window 4 in the dark-box main body 2 to completely block extraneous light. Instead, a camera (photography unit) 32 is provided in the dark-box main body 31 and a monitor 33 is provided outside the dark-box main body 31.

The camera 32 has a field of view large enough to allow both the objective lens 22 of the fluoroscopy unit 5 and the specimen A to be photographed simultaneously in the darkbox main body 31. Furthermore, the camera 32 is arranged opposite to the illumination light source 3 on the other side of the baffle plate 26 and is prevented from directly photographing the illumination light source 3. The camera 32 may be realized by a CMOS camera or a CCD camera. A CMOS camera has low power consumption, and is advantageous in terms of energy efficiency.

In the dark box apparatus for fluoroscopy 30 according to this embodiment, with the above-described structure, the interior of the dark-box main body 31 can be observed using the camera 32 and the monitor 33, even during fluoroscopy, with the aid of the illumination light source 3 emitting light L3 (not limited to visible light in this case) having the third spectral band B3, which does not interfere with fluoroscopy. This allows the observer to finely adjust the positional relationship between the fluoroscopy unit 5 and the specimen A during fluoroscopy, in the same manner as in the first embodiment.

With the dark box apparatus for fluoroscopy 30 according to this embodiment, the dark-box main body 31 may be provided with a plurality of cameras 32. This allows images from the plurality of cameras 32 to be observed by switching the screen on the single monitor 33. In this manner, the specimen A can be examined from a plurality of angles. This is advantageous in adjusting the positional relationship between the fluoroscopy unit 5 and the specimen A more accurately and easily.

Furthermore, in a case where the specimen A is a living organism, various items of information, such as vital information and temperature information, from several sensors (not shown in the figure) attached to the specimen A and the dark-box main body 31 may be simultaneously displayed on the monitor 33.

Figure 4:
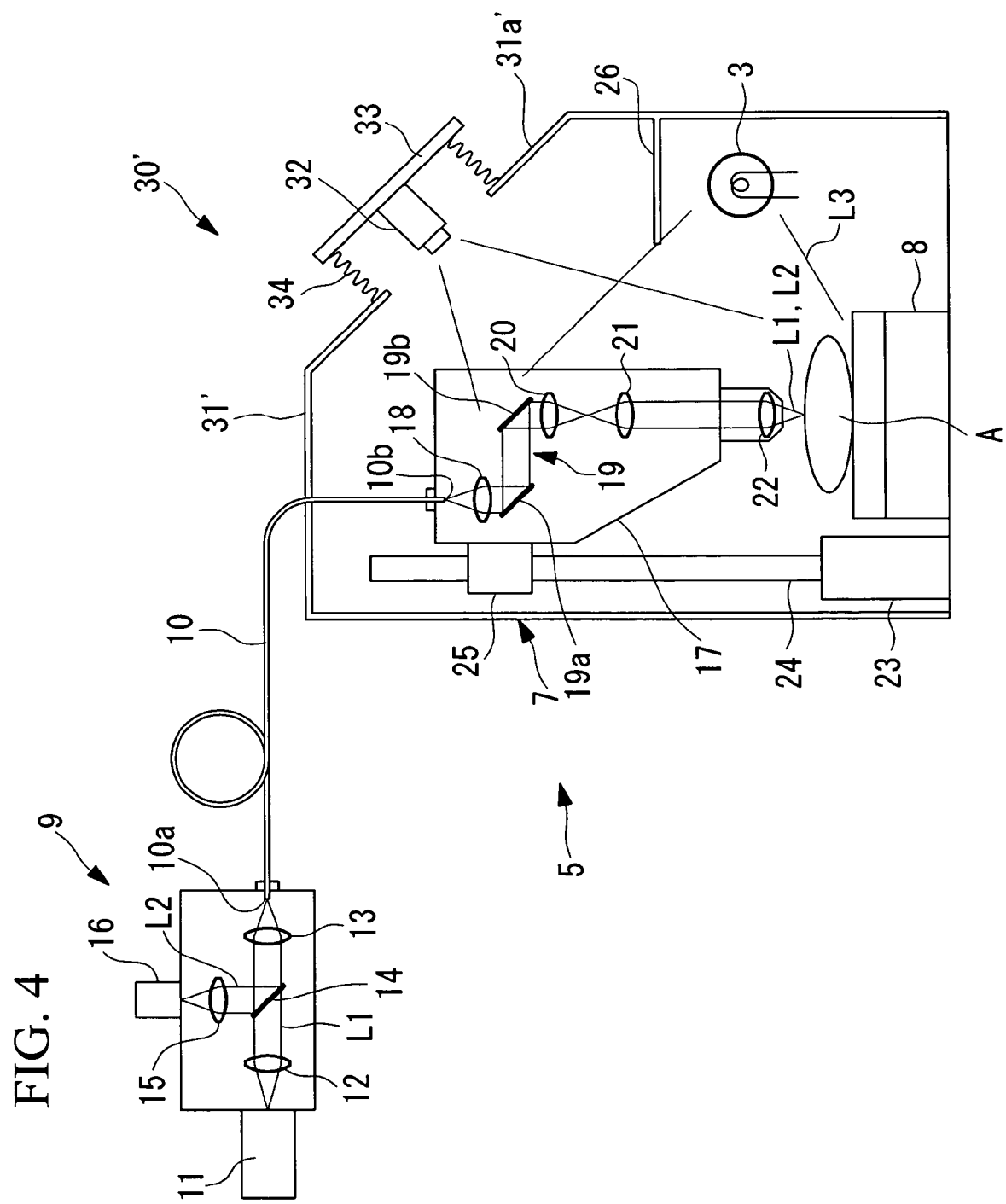
FIG. 4 is a longitudinal sectional view of a modification of the dark box apparatus for fluoroscopy shown in FIG. 3.

As shown in FIG. 4, a dark box apparatus for fluoroscopy 30' where the camera 32 is integrated with the monitor 33 by means of a wall surface 31a' of a dark-box main body 31' or the camera 32 is provided with the monitor 33 in some way may also be employed. In this case, the camera 32 is mounted so as to face the interior of the dark-box main body 31', whereas the monitor 33 is mounted so as to face the exterior of the dark-box main body 31', namely, opposite to the camera 32. In this manner, the observer of the monitor 33 can see into the dark-box main body 31' as if he or she were looking into the dark-box main body 2 through the observation window 4 of the dark box apparatus for fluoroscopy 1 according to the first embodiment. Therefore, the observer can perform adjustment of the examination head 6 and the stage 8 through remote operation while intuitively recognizing the movement direction and the amount of movement of the examination head 6 and the stage 8 on the monitor 33.

In addition, as shown in FIG. 4, the camera 32 provided or integrated with the monitor 33 may be secured on the wall surface 31a' of the dark-box main body 31' with bellows 34. The position of the camera 32 can be adjusted through deformation of the bellows 34, and a region to be examined can be adjusted within the deformation range of the bellows 34.

A fluoroscopy system 40 according to a third embodiment of the present invention will now be described with reference to FIG. 5.

The same components in this embodiment as those used in the dark box apparatuses 1 and 30 according to the first and second embodiments are denoted by the same reference numerals, and thus will not be described.

Figure 5:
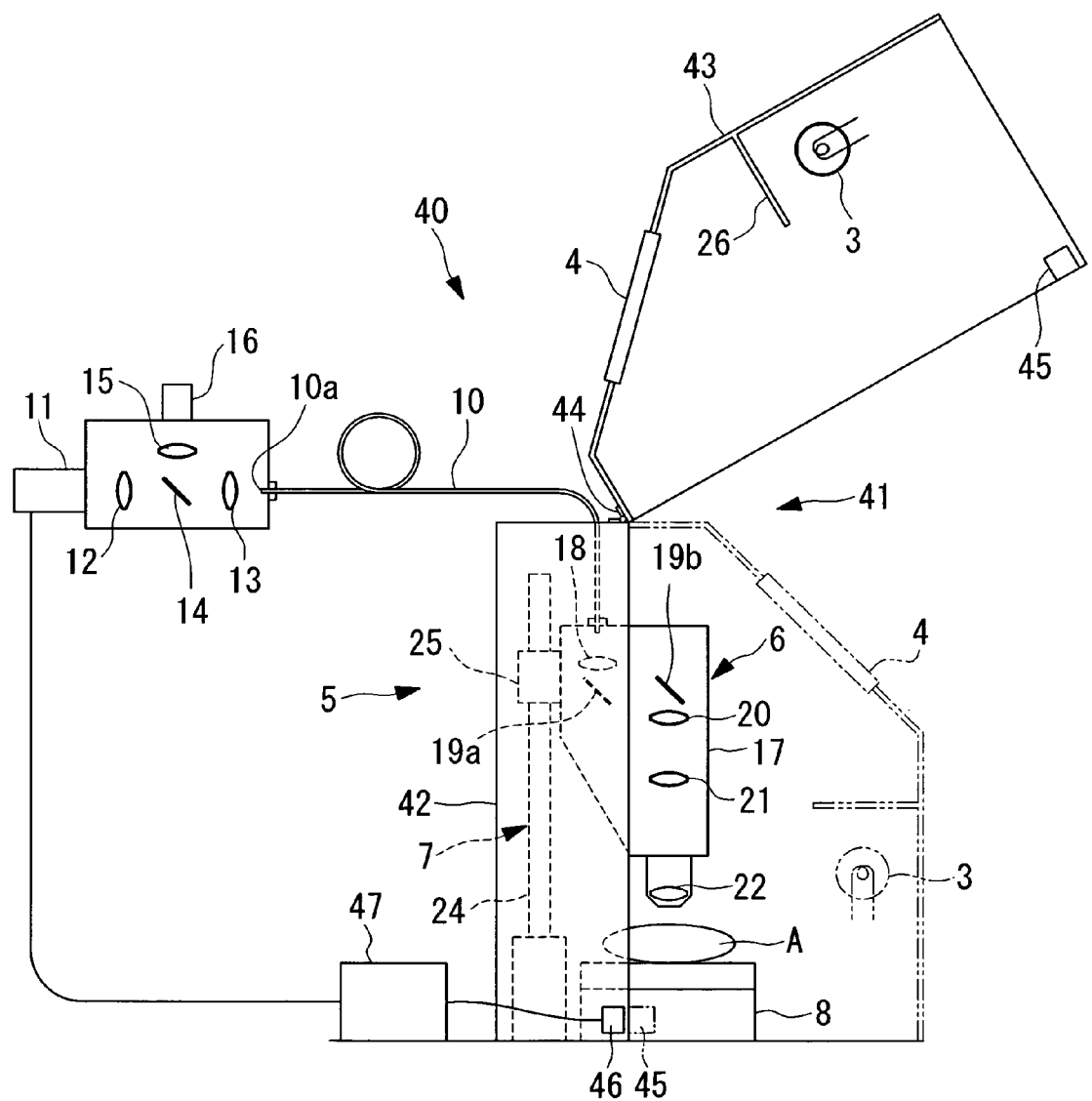
FIG. 5 is a longitudinal sectional view of a fluoroscopy system according to a third embodiment of the present invention.

Referring to FIG. 5, a fluoroscopy system 40 according to this embodiment includes the above-described fluoroscopy unit 5 and a dark box apparatus for fluoroscopy 41. As shown in FIG. 5, the dark box apparatus for fluoroscopy 41 is provided on a dark-box main body 42 such that a door 43 can be opened and closed with a hinge 44. The dark-box main body 42 is provided with an open/closed sensor 46 that can detect a detection member 45 on the door 43 when the door 43 is closed.

Furthermore, an excitation-light control unit 47 is connected to the open/closed sensor 46. When the door 43 is opened, the open state of the door 43 is detected by the excitation-light control unit 47 and the open/closed sensor 46. Since the detection member 45 goes out of the detection range of the open/closed sensor 46 at this time, the excitation light source 11 is turned OFF and stops the excitation light L1 from being emitted.

In the fluoroscopy system 40 according to this embodiment, with the above-described structure, when the door 43 is closed, the detection member 45 is detected by the open/closed sensor 46 and a signal indicating a closed state is sent to the excitation-light control unit 47. As a result, the excitation-light control unit 47 allows the excitation light source 11 to emit the excitation light L1. In the same manner as with the dark box apparatus for fluoroscopy 1 according to the first embodiment, the positional relationship between the fluoroscopy unit 5 and the specimen A is adjusted through the observation window 4 with the aid of the illumination light source 3 while fluoroscopy of the specimen A is in progress.

In this state, for the fluoroscopy system 40 according to this embodiment, when the door 43 of the dark-box main body 42 is opened for some reason, the open/closed sensor 46 is actuated to detect that the door 43 is in an open state. As a result, the excitation-light control unit 47 stops the excitation light source 11 from emitting the excitation light L1. In this manner, the excitation light L1 is prevented from leaking out of the dark-box main body 42. Consequently, fluoroscopy with the door 43 opened, which would cause extraneous light with various spectral bands to enter the dark-box main body 42, is prevented. Therefore, photographing a fluorescence image with a high degree of noise is avoided.

In this embodiment, the excitation light source 11 is prevented from emitting the excitation light L1 depending on the open/closed state of the door 43. Alternatively, a shutter (not shown in the figure) may be provided in front of the excitation light source 11 and the excitation light L1 may be turned ON/OFF according to open/close state of the shutter. Furthermore, when the door 43 is opened, the excitation light L1 may be blocked and the illumination light source 3 may be turned OFF. As a result of the illumination light source 3 being turned OFF while the dark-box main body 42 is observed through the observation window 4, the observer is informed of an open state of door 43 earlier.

Furthermore, a timer that is operatively associated with the operation of the open/closed sensor 46 may be provided to record information about the period of time for which the door 43 is open or to display such information on the monitor.

Figure 6:
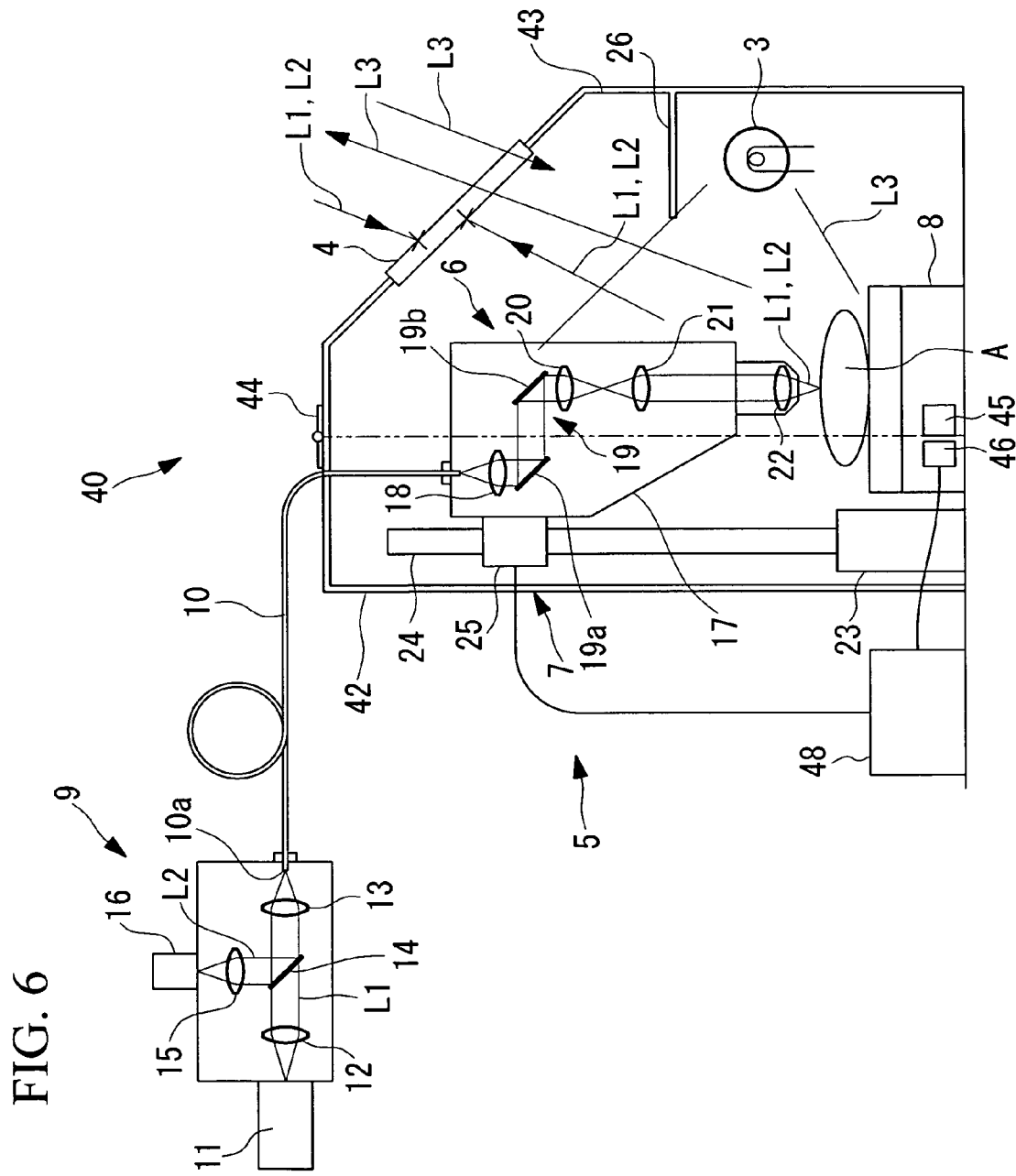
FIG. 6 is a longitudinal sectional view of a modification of the fluoroscopy system shown in FIG. 5.

In this embodiment, the excitation light source 11 is disabled when the door 43 is open. Instead of or in addition to this, an operation control unit 48 connected to the open/closed sensor 46 may be provided, as shown in FIG. 6. The operation control unit 48 is connected to, for example, the raising-and-lowering mechanism 7 of the examination head 6 or to the driving device of the stage 8, so that when the open/closed sensor 46 detects the closed state of the door 43, the operation speed in a closed state, such as the speed of the raising-and-lowering mechanism 7 in the dark-box main body 42, is preferably set to lower than the speed in an open state.

Although the interior of the dark-box main body 42 can be observed through the observation window 4, the amount of information acquired from the observation window 4 is restricted, and therefore, by setting the operation speed such as the speed of the raising-and-lowering mechanism 7 to a lower value while the door 43 is closed, the risk of damage to the specimen A and to the objective lens 22 due to interference between the specimen A and the objective lens 22 can be reduced.

What is claimed is:

1. A dark box apparatus for fluoroscopy comprising:
a dark-box main body enclosing a specimen and a fluoroscopy unit for illuminating the specimen with excitation light with a first spectral band and for detecting fluorescence with a second spectral band generated by the specimen;
an illumination light source disposed in the dark-box main body to emit light with a third spectral band different from the first spectral band and the second spectral band; and
an observation window disposed on the dark-box main body, the observation window being capable of transmitting light with a fourth spectral band which includes at least part of the third spectral band and does not include the first spectral band and the second spectral band.

2. The dark box apparatus for fluoroscopy according to claim 1, wherein the illumination light source is disposed at a location such that the illumination light source is not directly visible from outside through the observation window.

3. A dark box apparatus for fluoroscopy comprising:
a dark-box main body for blocking entry of extraneous light by enclosing a specimen and a fluoroscopy unit for illuminating the specimen with excitation light with a first spectral band and for detecting fluorescence with a second spectral band generated by the specimen;
an illumination light source disposed in the dark-box main body to emit light with a third spectral band different from the first spectral band and the second spectral band;
a photography unit disposed in the dark-box main body to photograph the specimen illuminated by the illumination light source and the fluoroscopy unit; and
an image display unit disposed outside the dark-box main body to display an image acquired by the photography unit.

4. The dark box apparatus for fluoroscopy according to claim 3, wherein the illumination light source is disposed at a location such that light emitted from the illumination light source is not directly incident upon the photography unit.

5. The dark box apparatus for fluoroscopy according to claim 3, wherein a camera including the photography unit and the image display unit is provided on a wall surface of the dark-box main body such that the photography unit faces inward and the image display unit faces outward.

6. The dark box apparatus for fluoroscopy according to claim 5, further comprising:
a bellows member between the wall surface of the dark-box main body and the camera, the bellows member supporting the camera so that the camera is movable relative to the wall surface.

7. The dark box apparatus for fluoroscopy according to claim 1, wherein the illumination light source includes a wavelength-switching mechanism for switching a spectral band of emitted light.

8. The dark box apparatus for fluoroscopy according to claim 3, wherein the illumination light source includes a wavelength-switching mechanism for switching a spectral band of emitted light.

9. A fluoroscopy system comprising:
a fluoroscopy unit for illuminating a specimen with excitation light with a first spectral band and for detecting fluorescence with a second spectral band generated by the specimen; and
the dark box apparatus for fluoroscopy according to claim 1, wherein
the dark-box main body includes:
a door for opening and closing the dark-box main body;
an open/closed sensor for detecting an open/closed state of the door; and
an excitation-light control section for stopping emission of excitation light from the fluoroscopy unit when the open/closed sensor detects that the door is opened.

10. A fluoroscopy system comprising:
a fluoroscopy unit for illuminating a specimen with excitation light with a first spectral band and for detecting fluorescence with a second spectral band generated by the specimen; and
the dark box apparatus for fluoroscopy according to claim 1, wherein
the dark-box main body includes:
a door for opening and closing the dark-box main body;
an open/closed sensor for detecting an open/closed state of the door; and
an operation control section for decreasing an operation speed of the fluoroscopy unit when the open/closed sensor detests that the door is closed.

11. A fluoroscopy method for emitting excitation light with a first spectral band from a fluoroscopy unit onto a specimen and for examining fluorescence with a second spectral band emitted from the specimen, the method comprising steps of:
enclosing the specimen and the fluoroscopy unit with a dark box;
emitting light with a third spectral band different from the first spectral band and the second spectral band in the dark box; and
manipulating the specimen or the fluoroscopy unit from outside the dark box while observing light with the third spectral band outside the dark box through an observation window, disposed in the dark box, capable of transmitting light with a fourth spectral band which includes at least part of the third spectral band and does not include the first spectral band and the second spectral band or through a photography unit disposed in the dark box.

* * * * *